United States Patent
Sharma

(10) Patent No.: US 10,077,225 B2
(45) Date of Patent: *Sep. 18, 2018

(54) SYNTHESIS OF INTERMEDIATE FOR TREPROSTINIL PRODUCTION

(71) Applicant: United Therapeutics Corporation, Silver Spring, MD (US)

(72) Inventor: Vijay Sharma, Olney, MD (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/440,441

(22) Filed: Feb. 23, 2017

(65) Prior Publication Data

US 2017/0197898 A1 Jul. 13, 2017

Related U.S. Application Data

(63) Continuation of application No. 14/689,244, filed on Apr. 17, 2015, now Pat. No. 9,611,206, which is a continuation of application No. 14/002,446, filed as application No. PCT/US2012/027234 on Mar. 1, 2012, now abandoned.

(60) Provisional application No. 61/448,317, filed on Mar. 2, 2011.

(51) Int. Cl.
   *C07C 45/42* (2006.01)
   *C07C 213/08* (2006.01)
   *C07F 1/08* (2006.01)
   *C07C 47/57* (2006.01)
   *C07C 45/68* (2006.01)
   *C07C 47/575* (2006.01)

(52) U.S. Cl.
   CPC ............ *C07C 45/42* (2013.01); *C07C 45/68* (2013.01); *C07C 47/575* (2013.01); *C07C 213/08* (2013.01); *C07F 1/08* (2013.01)

(58) Field of Classification Search
   None
   See application file for complete search history.

(56) References Cited

U.S. PATENT DOCUMENTS

| | | | |
|---|---|---|---|
| 4,306,075 A | 12/1981 | Aristoff | |
| 4,306,076 A | 12/1981 | Nelson | |
| 4,424,376 A | 1/1984 | Moniot et al. | |
| 4,463,183 A | 7/1984 | Haslanger | |
| 4,486,598 A | 12/1984 | Aristoff | |
| 4,544,764 A | 10/1985 | Aristoff | |
| 4,668,814 A | 5/1987 | Aristoff | |
| 4,683,330 A | 7/1987 | Aristoff | |
| 5,039,814 A | 8/1991 | Shuman et al. | |
| 5,153,222 A | 10/1992 | Tadepalli et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,765,117 B2 | 7/2004 | Moriarty et al. | |
| 6,803,386 B2 | 10/2004 | Shorr et al. | |
| 6,809,223 B2 | 10/2004 | Moriarty et al. | |
| 6,933,385 B2 | 8/2005 | Westermann et al. | |
| 7,199,157 B2 | 4/2007 | Wade et al. | |
| 7,384,978 B2 | 6/2008 | Phares et al. | |
| 7,417,070 B2 | 8/2008 | Phares et al. | |
| 7,544,713 B2 | 6/2009 | Phares et al. | |
| 7,879,909 B2 | 2/2011 | Wade et al. | |
| 7,999,007 B2 | 8/2011 | Jeffs et al. | |
| 8,461,393 B2* | 6/2013 | Sharma | C07C 45/42 568/433 |
| 9,611,206 B2* | 4/2017 | Sharma | C07C 51/00 |
| 2002/0173672 A1 | 11/2002 | Moriarty et al. | |
| 2003/0166728 A1* | 9/2003 | Shorr | A61K 31/557 514/569 |
| 2004/0176645 A1 | 9/2004 | Moriarty et al. | |
| 2005/0085540 A1 | 4/2005 | Phares et al. | |

(Continued)

FOREIGN PATENT DOCUMENTS

CA 2 710 726 A1 1/2012
CN 101891596 A 11/2010

(Continued)

OTHER PUBLICATIONS

Moriarty ("The intramolecular Asymmetric Pauson-Khand Cyclization as a Novel and General Stereoselective Route to Benzindene Prostacyclins: Synthesis of UT-15 (Treprostinil)" J. Org. Chem. 2004, vol. 69, p. 1890-1902).*
Alexander et al., "The Synthesis of Benzindene Prostacyclin Analogs as Potential Antiulcer Agents," Prostaglandins, 1986, 32(5):647-653.
Aristoff et al., "Synthesis and Structure-Activity Relationship of Novel Stable Prostacyclin Analogs," Advances in Prostaglandin, Thromboxane, and Leukotriene Research, Samuelsson et al., ,Eds., 1983, 11:267-274.
Aristoff et al., "Synthesis of Benzopyran Prostaglandins, Potent Stable Prostacyclin Analogs, Via an Intramolecular Mistunobu Reaction," Tetrahedron Letters, 1984, 25(36):3955-3958.
Aristoff et al., "Total Synthesis of a Novel Antiulcer Agent via a Modification of the Intramolecular Wadsworth-Emons-Wittig Reaction," J. Am. Chem. Soc., 1985, 107:7967-7974.

(Continued)

*Primary Examiner* — Jafar Parsa
*Assistant Examiner* — Amy C Bonaparte
(74) *Attorney, Agent, or Firm* — Foley & Lardner LLP

(57) ABSTRACT

The compound according to Formula I is an intermediate in the synthesis of prostacylin analogs. The present invention provides an efficient method for synthesizing a Formula I compound.

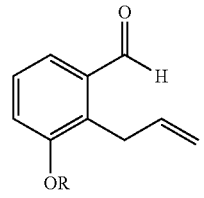

17 Claims, No Drawings

(56) References Cited

U.S. PATENT DOCUMENTS

| | | | |
|---|---|---|---|
| 2005/0101608 | A1 | 5/2005 | Santel |
| 2005/0165111 | A1 | 7/2005 | Wade et al. |
| 2005/0282901 | A1 | 12/2005 | Phares et al. |
| 2005/0282903 | A1 | 12/2005 | Wade et al. |
| 2007/0078095 | A1 | 4/2007 | Phares et al. |
| 2007/0078182 | A1 | 4/2007 | Phares et al. |
| 2007/0082948 | A1 | 4/2007 | Phares et al. |
| 2008/0200449 | A1 | 8/2008 | Olschewski et al. |
| 2008/0249167 | A1 | 10/2008 | Phares et al. |
| 2008/0280986 | A1 | 11/2008 | Wade et al. |
| 2009/0036465 | A1 | 2/2009 | Roscigno et al. |
| 2009/0124697 | A1 | 5/2009 | Cloutier et al. |
| 2009/0163738 | A1 | 6/2009 | Batra et al. |
| 2009/0281189 | A1 | 11/2009 | Walsh |
| 2010/0076083 | A1 | 3/2010 | Olschewski |
| 2010/0282622 | A1 | 11/2010 | Phares |
| 2011/0092599 | A1 | 4/2011 | Wade et al. |
| 2011/0118213 | A1 | 5/2011 | Phares et al. |
| 2011/0144204 | A1 | 6/2011 | Jeffs et al. |
| 2011/0224236 | A1 | 9/2011 | Rothblatt et al. |
| 2011/0319641 | A1 | 12/2011 | Batra et al. |
| 2012/0004307 | A1 | 1/2012 | Wade et al. |
| 2012/0010159 | A1 | 1/2012 | Rothblatt et al. |
| 2012/0197041 | A1 | 8/2012 | Batra et al. |
| 2012/0226076 | A1 | 9/2012 | Sharma |

FOREIGN PATENT DOCUMENTS

| | | |
|---|---|---|
| CN | 101891715 A | 11/2010 |
| EP | 0 004 335 A2 | 10/1979 |
| EP | 0 087 237 B1 | 5/1986 |
| EP | 0 175 450 B1 | 3/1989 |
| EP | 0 159 784 B1 | 6/1989 |
| EP | 0 496 548 A1 | 7/1992 |
| WO | WO 98/39337 A1 | 9/1998 |
| WO | WO 99/21830 A1 | 5/1999 |
| WO | WO 03/070163 A2 | 8/2003 |
| WO | WO 2005/007081 A2 | 1/2005 |
| WO | WO 2007/134292 A2 | 11/2007 |
| WO | WO 2008/100977 A2 | 8/2008 |
| WO | WO 2009/117095 A1 | 9/2009 |
| WO | WO 2012/009816 A1 | 1/2012 |

OTHER PUBLICATIONS

Batra et al., "Crystallization Process Development for a Stable Polymorph of Treprostinil Diethanolamine (UT-15C) by Seeding," Organic Process Research & Development, 2009, 13:242-249.

Belch et al., "Randomized, Double-Blind, Placebo-Controlled Study Evaluating the Efficacy and Safety of AS-013, a Prostaglandin E1 Prodrug, in Patients with Intermittent Claudication," Circulation, May 6, 1997, 95 (9):2298-2302.

Chemburkar et al, "Dealing with the Impact of Ritonavir Polymorphs on the Late Stages of Bulk Drug Process Development," Organic Process Research & Development, 2000, 4:413-417.

Chung et al., "Promoters for the (Alkyne)hexacarbonyldicobalt-Based Cyclopentenone Synthesis," Organometallics, 1993, 12:220-223.

Clark et al., "High-Performance Liquid Chromatographic Method for Determining the Enantiomeric Purity of a Benzindene Prostaglandin by a Diastereomeric Separation," Journal of Chromatography, 1987, 408:275-283.

Comins et al., "Ortho Metalation Directed by β-Amino Alkoxides," J. Org. Chem., 1984, 49:1078-1083.

Comins et al., "Ortho Substitution of M-Anisaldehyde via α-Amino Alkoxide Directed Lithiation," J. Org. Chem., 1989, 54:3730-3732.

Corey et al. "Novel Electronic Effects of Remote Substituents on the Oxazaborolidine-Catalyzed Enantioselective Reduction of Ketones," Tetrahedron Letters, 1995, 36(50):9153-9156.

Greene, TW, et al., "Protecting Groups," 1991, 1-11.

Hardinger et al., "Triply-Convergent Syntheses of Two Homochiral Arene-Fused Prostacyclin Analogs Related to U68,215," Bioorganic & Medicinal Chemistry Letters, 1991, 1(1):79-82.

Hicks et al., "A Practical Titanium-Catalyzed Synthesis of Bicyclic Cyclopentenones and Allylic Amines," J. Org. Chem., 1996, 61:2713-2718.

Jeong et al., "Catalytic Version of the Intramolecular Pauson-Khand Reaction," J. Am. Chem. Soc., 1994, 116:3159-3160.

Khand et al., "Organocobalt Complexes. Part II Reaction of Acetylenehexacarbonyl-dicobalt Complexes, $(R^1C_2R^2)Co_2(CO)_8$, with Norbornene and its Derivatives," J. Chem. Soc., J.C.S. Perkin I., 1973, 977-981.

Mathre et al., "A Practical Enantioselective Synthesis of α,α-Diaryl-2-pyrrolidinemethanol. Preparation and Chemistry of the Corresponding Oxazaborolidines," J. Org. Chem., 1991, 56:751-762.

Mmutlane et al., "The synthesis of ventiloquinone L, the monomer of cardinalin 3," Org. Biomol. Chem., 2004, 2:2461-2470.

Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem. 2004, 69, 1890-1902.

Mullin, John W., "Crystallization and Precipitation," Ullmann's Encyclopedia of Industrial Chemistry, 2002, 1-51.

Mulzer et al., "Asymmetric Synthesis of Carbacyclin Precursors by Pauson-Khand Cyclization," Liebigs Ann. Chem., 1988, 891-897.

Nelson, Norman A., "Prostaglandin Nomenclature," J. Med. Chem., Sep. 1974, 17(9):911-918.

Pagenkopf et al., "Photochemical Promotion of the Intramolecular Pauson-Khand Reaction. A New Experimental Protocol for Cobalt-Catalyzed [2+2+1] Cycloadditions," J. Am. Chem. Soc., 1996, 118:2285-2286.

Pagenkopf, Brian L., "Substrate and Reagent Control of Diastereoselectivity in Transition Metal-Mediated Process: Development of a Catalytic Photo Promoted Pauson-Khand Reaction," Diss. Abstr. Int., 57(12):7535, 1977, Abstract.

Pansegrau et al., "The Oxazoline-Benzyne Route to 1,2,3-Trisubstituted Benzenes. Tandem Addition of Organolithiums, Organocuprates, and α-Lithionitriles to Benzynes," J. Am. Chem. Soc., 1988, 110:7178-7184.

Patterson et al., "Acute Hemodynamic Effects of the Prostacyclin Analog 15AU81 in Severe Congestive Heart Failure," Am. J. Cardio., 1995, 75:26A-33A.

Pauson, Peter L., "The Khand Reaction," Tetrahedron, 1985, 41(24):5855-5860.

Rowley et al., "Application of the Pauson-Khand reaction to the synthesis of pentalenic acid," Journal of Organometallic Chemistry, 1991, 413:C5-C9.

Schore, Neil E., "Transition-Metal-Mediated Cycloaddition Reactions of Alkynes in Organic Synthesis," Chem. Rev., 1988, 88:1081-1119.

Shambayati et al., "N-Oxide Promjoted Pauson-Khand Cyc izations at Room Temperature," Tetrahedron Letters, 1990, 31(37):5289-5292.

Snell et al., "Investigating the Effect of Impurities on Macromolecule Crystal Growth in Microgravity," Crystal Growth & Design, 2001, 1(2):151-158.

Sorbera et al. "UT-15. Treatment of Pulmonary Hypertension Treatment of Peripheral Vascular Disease," Drug of the Future, 2001, 26(4), 364-374.

Takano et al., "Enantiodivergent Synthesis of Both Enantiomers of Sulcatol and Matsutake Alcohol from (R)-Epichlorohydrin," Chemistry Letters, 1987, 2017-2020.

Viedma, Cristobal, "Selective Chiral Symmetry Breaking during Crystallization: Parity Violation of Cryptochiral Environment in Control?" Crystal Growth & Design, 2007, 7(3):553-556.

Whittle et al., "Antithrombotic Assessment and Clinical Potential of Prostacyclin Analogues," Progress in Medicinal Chemistry, Ellis et al. Eds., 1984, Chapter 6, vol. 21, 238-279.

Zhang et al., "A Nickel(0)-Catalyzed Process for the Transformation of Enynes to Bicyclic Cyclopentenones," J. Org. Chem., 1996, 61:4498-4499.

* cited by examiner

SYNTHESIS OF INTERMEDIATE FOR TREPROSTINIL PRODUCTION

RELATED APPLICATIONS

The present application is a Continuation of U.S. application Ser. No. 14/689,244, filed Apr. 17, 2015, which is a Continuation of U.S. application Ser. No. 14/002,446, which is the U.S. National Stage of PCT/US2012/027234, filed Mar. 1, 2012, which claims priority to U.S. provisional application No. 61/448,317 filed Mar. 2, 2011, which are incorporated herein by reference in their entirety.

FIELD

The present application relates generally to the field of pharmaceutical production and more specifically to methods of synthesizing an intermediate for producing prostacyclin derivatives, such as Treprostinil.

SUMMARY

One embodiment is a method for synthesizing a compound according to Formula I.

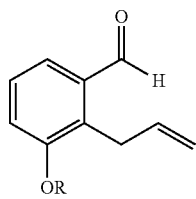

I

According to the method, the compound of Formula I may be synthesized by hydrolyzing a compound represented by Formula A.

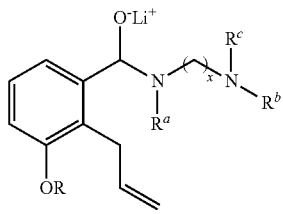

A

For Formula A compounds, "x" may be an integer between 0 and 4 inclusive. Substituent R may be selected from the group consisting of H, straight or branched ($C_1$-$C_6$)alkyl, ($C_6$-$C_{14}$)aryl, and ($C_6$-$C_{14}$)aryl($C_1$-$C_6$)alkylene-, while substituent groups $R^a$, $R^b$ and $R^c$ are each independently selected from the group consisting of H, straight or branched ($C_1$-$C_6$)alkyl, ($C_3$-$C_6$)cycloalkyl, ($C_3$-$C_{14}$)aryl, ($C_3$-$C_{14}$)aryl($C_1$-$C_6$)alkylene- and ($C_3$-$C_6$)cycloalkyl($C_1$-$C_6$)alkylene-.

In some embodiments, the hydrolysis of a Formula A compound may be accomplished by contact with water, aqueous mineral acid, or an aqueous solution of sodium sulfite.

Another embodiment may be a method for synthesizing a Formula A compound. Such synthesis may be accomplished by contacting a Formula B compound with an organolithium reagent, such as phenyllithium or butyllithium to form an otho-lithiated intermediate which may be converted to a cuprate using copper cyanide.

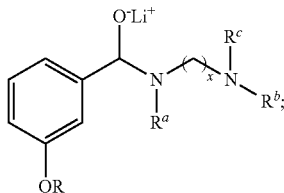

B

The obtained cuprate may be then contacted with an allyl halide, for example, with an allyl chloride, an allyl bromide, or an allyl iodide synthesize a compound according to Formula A.

In some embodiments, $R^a$, $R^b$ and $R^c$ may be each independently ($C_1$-$C_6$)alkyl and "x" is 2. In one embodiment, $R^a$, $R^b$ and $R^c$ are each methyl and "x" is 2.

R may be an alcohol protecting group, straight or branched ($C_1$-$C_6$)alkyl; ($C_6$-$C_{14}$)aryl and ($C_6$-$C_{14}$)aryl($C_1$-$C_6$)alkylene-. For example, R may be selected from methyl, ethyl, propoyl, isopropyl, butyl, iso-butyl, tert-butyl, pentyl, neo-pentyl, hexyl and branched hexyl. For example, in one embodiment substituent R may be methyl. Alternatively, R may be a ($C_6$-$C_{14}$)aryl($C_1$-$C_6$)alkylene-, for example a benzyl group.

The allylating agent may be, for example, an allyl halide, such as an allyl bromide or an allyl iodide, although other allylating reagents may also be used.

Yet another embodiment may be a method for synthesizing a Formula I compounds, which may include the following:

(a) contacting an aldehyde represented by Formula C with a compound selected from the group consisting of $R^a$—$NH_2$, $R^a R^b N$—$(CHR')_x$—$NHR^a$ and R'—OH in the presence of an organolitium;

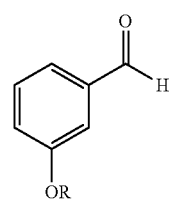

C (b) contacting the product from step (a) with an organolithium to form an ortho-lithiated product which is contacted with copper cyanide to form a cuprate;

(c) contacting the cuprate from step (b) with an allyl halide selected from the group consisting of allyl chloride, allyl bromide and allyl iodide to form a Formula A compound which is hydrolyzed to give a Formula I compound.

DETAILED DESCRIPTION

Unless otherwise specified, "a" or "an" means one or more.

(+)-Treprostinil (also known as UT-15) is the active ingredient in Remodulin®, a commercial drug approved by FDA for the treatment of pulmonary arterial hypertension (PAH). It was first described in U.S. Pat. No. 4,306,075.

Treprostinil is a stable analog of prostacyclin (PGI$_2$) belonging to a class of compounds known as benzindene prostacyclins, which are useful pharmaceutical compounds possessing activities such as platelet aggregation inhibition, gastric secretion reduction, lesion inhibition, and bronchodilation.

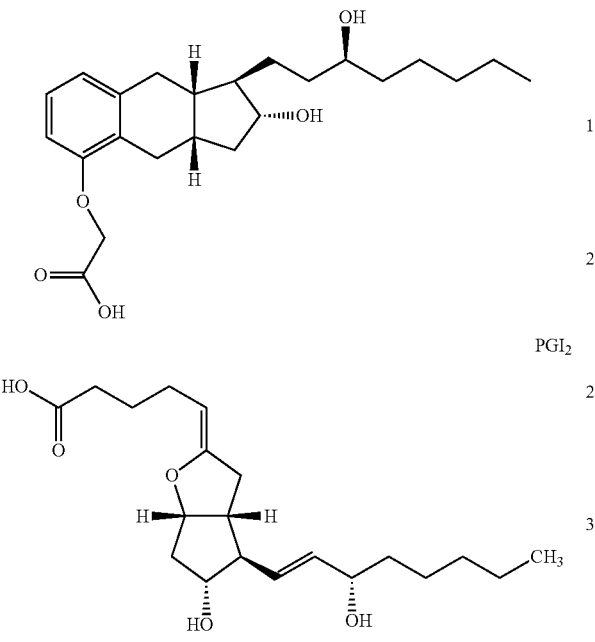

U.S. Pat. Nos. 5,153,222, 6,054,486; 6,521,212; 6,756,033; 6,803,386; 7,199,157; 7,879,909 and 7,999,007 as well as U.S. patent application publications Nos. 2005/0165111; 2008/0200449; 2008/0280986; 2009/0124697; 2009/0281189; 2009/0036465; 2010/0076083; 2010/0282622; 2011/0092599; 2011/0144204; 2011/0224236; 2012/0004307 and 2012/0010159 disclose various applications of treprostinil. U.S. Pat. Nos. 7,417,070, 7,384,978 and 7,544,713 as well as U.S. publications Nos. 2005/0282901; 2007/0078095; 2008/0249167 and 2011/0118213 describe oral formulations of treprostinil and other prostacyclin analogs as well as their use for treatment of a variety of conditions.

The following documents provide information, which may be useful for preparing treprostinil and/or other prostacyclin derivatives: Moriarty, et al in *J. Org. Chem.* 2004, 69, 1890-1902, *Drug of the Future*, 2001, 26(4), 364-374, Aristoff et al. JACS 107(26), 1985, 7967-74; Aristoff et al. Advances in Prostaglandin, Thromboxane and Leukotriene Research, vol. 11, 267, 1983; U.S. Pat. Nos. 4,306,075, 4,668,814; 4,683,330; 6,441,245, 6,528,688, 6,700,025, 6,765,117, 6,809,223; US Publications Nos. 2009/0163738 and 2011/0319641 as well as PCT publication WO2012009816.

A compound of Formula I may be a key intermediate in the syntheses of (+) Treprostinil and other prostacyclin derivatives, such as the ones disclosed in U.S. Pat. Nos. 6,441,245, 6,528,688, 6,700,025, 6,765,117, 6,809,223 and US Publications Nos. 2009/0163738 and 2011/0319641 as well as PCT publication WO2012009816:

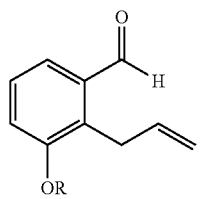

The present inventor developed a novel method for synthesizing a Formula I compound. Specifically, the inventor provide a synthesis for Formula I compounds, which may be performed efficiently in one pot using commercially available starting materials.

Definitions

In the context of the present invention, "alkyl" refers to straight, branched chain, or cyclic hydrocarbyl groups including from 1 to about 20 carbon atoms. For instance, an alkyl can have from 1 to 10 carbon atoms or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at one or more positions, for example, 1, 2, 3, 4, 5, or even 6 positions, which substituents are attached at any available atom to produce a stable compound, with substitution as described herein. "Optionally substituted alkyl" refers to alkyl or substituted alkyl.

"Alkene" refers to straight, branched chain, or cyclic hydrocarbyl groups including from 2 to about 20 carbon atoms having 1-3, 1-2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene. The terms "allyl" or "allylene" belongs to the genus "alkene" and refers to a compound having the following generic structure CH$_2$=CH—CH$_2$—. Suitable allylating reagents include without limitation allyl chloride, allyl bromide, allyl iodide, allyl carbonate, allyl alcohol and allyl diphenylphosphine oxide.

The term "alkenylene" refers to divalent alkene. Examples of alkenylene include without limitation, ethenylene (—CH=CH—) and all stereoisomeric and conformational isomeric forms thereof "Substituted alkenylene" refers to divalent substituted alkene. "Optionally substituted alkenylene" refers to alkenylene or substituted alkenylene.

Each of the terms "halogen," "halide," and "halo" refers to —F, —Cl, —Br, or —I.

The term "aryl," alone or in combination refers to an aromatic monocyclic or bicyclic ring system such as phenyl or naphthyl. "Aryl" also includes aromatic ring systems that are optionally fused with a cycloalkyl ring, as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

A "hydroxyl" or "hydroxy" refers to an —OH group.

The term "alkoxy" refers to an —O-alkyl group having the indicated number of carbon atoms. For example, a $(C_1-C_6)$alkoxy group includes —O-methyl, —O-ethyl, —O-propyl, —O-isopropyl, —O-butyl, —O-sec-butyl, —O-tert-butyl, —O-pentyl, —O-isopentyl, —O-neopentyl, —O-hexyl, —O-isohexyl, and —O-neohexyl.

The term "$(C_3-C_{14})$aryl-$(C_1-C_6)$alkylene" refers to a divalent alkylene wherein one or more hydrogen atoms in the $C_1-C_6$ alkylene group is replaced by a $(C_3-C_{14})$aryl group. Examples of $(C_3-C_{14})$aryl-$(C_1-C_6)$alkylene groups include without limitation 1-phenylbutylene, phenyl-2-butylene, 1-phenyl-2-methylpropylene, phenylmethylene, phenylpropylene, and naphthylethylene.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 3$^{rd}$ ed.; Wiley: N.Y., 1999). Suitable alcohol protecting groups are well know in the chemical art, and include without limitation actetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or triisopropylsilyl (TIPS) ether), tetrahydropyranyl (THP), methyl ether and ethoxyethyl ether.

The term "cycloalkyl" refer to monocyclic, bicyclic, tricyclic, or polycyclic, 3- to 14-membered ring systems, which are either saturated, unsaturated or aromatic. The heterocycle may be attached via any atom. Cycloalkyl also contemplates fused rings wherein the cycloalkyl is fused to an aryl or heteroaryl ring as defined above. Representative examples of cycloalkyl include, but are not limited to cyclopropyl, cycloisopropyl, cyclobutyl, cyclopentyl, cyclohexyl, cyclopropene, cyclobutene, cyclopentene, cyclohexene, phenyl, naphthyl, anthracyl, benzofuranyl, and benzothiophenyl. A cycloalkyl group can be unsubstituted or optionally substituted with one or more substituents as described herein below.

The term "cycloalkylene" refers to divalent cycloalkylene. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The present compounds may exist in various isomeric forms, including configurational, geometric, and conformational isomers, including, for example, cis- or trans-conformations. The present compounds may also exist in one or more tautomeric forms, including both single tautomers and mixtures of tautomers. The term "isomer" is intended to encompass all isomeric forms of a compound of this invention, including tautomeric forms of the compound. All forms are included in the invention.

Some compounds described here may have asymmetric centers and therefore exist in different enantiomeric and diastereomeric forms. A compound of the invention may be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention may be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

Methods for Synthesizing Formula I Compounds

The present application relates to a compound according to Formula I and to methods for making Formula I compounds.

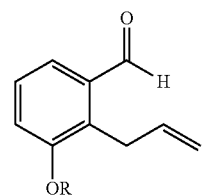

I

For Formula I compounds R may be an alcohol protecting group or R may be selected from the group consisting of H, straight or branched $(C_1-C_6)$alkyl, $(C_6-C_{14})$aryl and $(C_6-C_{14})$aryl$(C_1-C_6)$alkylene-. For example, R may be one of the alcohol protecting groups disclosed above. In some embodiments, R may be selected from the group consisting of acetyl, benzoyl, benzyl, p-methoxyethoxymethyl ether, methoxymethyl ether, dimethoxytrityl, p-methoxybenzyl ether, trityl, silyl ether (e.g., trimethylsilyl (TMS), tert-butyldimethylsilyl (TBMDS), tert-butyldimethylsilyloxymethyl (TOM) or triisopropylsilyl (TIPS) ether), tetrahydropyranyl (THP), methyl ether and ethoxyethyl ether. In some embodiments, R may be methyl, p-methoxybenzyl or benzyl.

Also contemplated is a facile and efficient synthesis for Formula I compounds. Although, synthesis of a Formula I compound by direct allylation of a meta-substituted arylaldehyde which was protected as an imine has been carried out, gas chromatography analysis showed the obtained product to be a mixture of three components, namely, a Formula I compound and a mixture of its positional regioisomers depicted below as compounds (A) and (B).

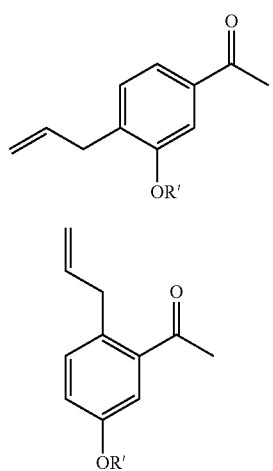

While the above process simplified synthesis of a Formula I, the obtained product contained the desired Formula I compound as well as undesired regioisomers. In an attempt to improve yields and eliminate undesired side products, the present inventor undertook a study to develop an alternate methodology for synthesizing a Formula I compound. In one embodiment, therefore, is provided a one pot synthesis for a Formula I compound.

The overall protocol is illustrated in Scheme 1. Synthesis of the target compound according to the inventive process may begin with the in-situ protection of aldehyde (6) using, for example, N,N,N-trimethylethylene diamine in the presence of phenyllithium or butyllithium to give (6a). Ortho-lithiation of the protected aldehyde (6a) may follow conversion of the ortho-lithiated intermediate to the corresponding cuprate (6c), and allylation may give intermediate (6d) which may be hydrolyzed in-situ to afford the target compound (7). As illustrated below, the conversion of lithiated intermediate (6b) to the corresponding cuprate (6c) helps to improve yield by stabilizing the ortho-anion and promoting allylation.

Scheme 1

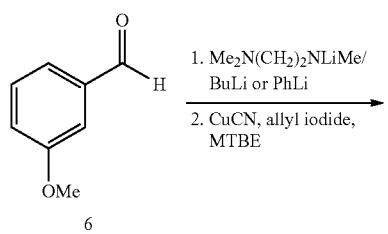

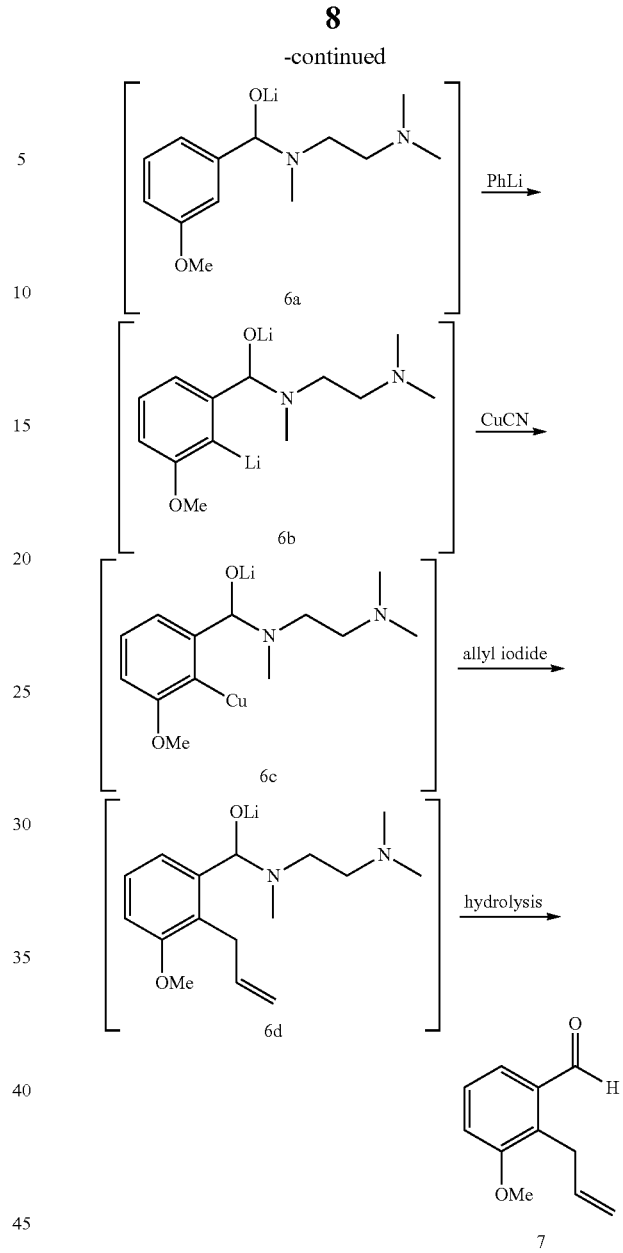

There are several advantages of the present method over previous synthetic processes for making a Formula I compound. For example, the target compound may be synthesized by the direct allylation of an appropriately substituted commercially available aldehyde. Because synthesis is achieved in "one-pot," there is no need to isolate and purify intermediates. Accordingly, the present method may reduce the overall number of synthetic steps, save time and avoid the use of extra chemicals, manpower, and large volume of solvents. Another advantage of the present method may be that it may permit the synthesis to be carried out at ambient temperature (no need for cryogenic equipment), and eliminates tedious column chromatographic purifications. Moreover, the yield and chemical purity of the desired product is greatly improved.

Other differences between the inventive process for ortho-lithiation of aromatic aldehydes and processes disclosed in the prior art (e.g., Comins et al., *J. Org. Chem.*, 1984, 49, 1078 and *J. Org. Chem.*, 1989, 54, 3730), are the stabilization of ortho-lithiated anion intermediate by copper cyanide (3c, scheme 2), and the use of solvent MTBE in place of THF as the solvent. The present inventor also found allyl iodide to be a better allylating reagent than allyl bromide used in many prior art processes. Based on these initial observations, a study was undertaken in which the following parameters listed in Table 1 were altered for improving the synthesis of a Formula I compound.

TABLE 1

Tabular summary of variable parameters

| S. No. | Parameters | Option 1 | Option 2 | Option 3 |
|---|---|---|---|---|
| 1 | Solvent | Toluene | THF | MTBE |
| 2 | Lithium Reagent | n-Butyl lithium (2.5M in hexanes) | Phenyl lithium (1.8M in dibutyl ether) | Combination of option 1 & 2 |

TABLE 1-continued

Tabular summary of variable parameters

| S. No. | Parameters | Option 1 | Option 2 | Option 3 |
|---|---|---|---|---|
| 3 | Temperature and Time of the reaction | ≤0° C. to Ambient (≥16 hours) | Ambient (≥16 hours) | Ambient to 35 ± 2° C. (≤10 hours) |
| 4 | Allylating reagent | Allyl bromide | Allyl iodide | NA |
| 5 | Copper Cyanide | Presence of CuCN | Absence of CuCN | NA |
| 6 | Purification procedure | NaHSO$_3$ method | Distillation method | Column chromatography |

A total of fourteen experiments were carried out to identify experimental parameters that provided the target compound in high yield and purity. The experimental details are set forth in Table 2a-2c below.

TABLE 2a

Details of experiments

| Experimental Parameters | Experiment 1 | Experiment 2 | Experiment 3 | Experiment 4 | Experiment 5 |
|---|---|---|---|---|---|
| Lot number | R-UT-1041-197 | R-UT-1041-198A | R-UT-1041-198B | R-UT-1059-001 | R-UT-1059-004 |
| Scale | 100 mg | 100 mg | 100 mg | 100 mg | 100 mg |
| Allylating agent | Allyl bromide | Allyl bromide | Allyl bromide | Allyl bromide | Allyl bromide |
| Reaction Temp | ≤0° C. | ≤0° C. | ≤0° C. | ≤0° C. | ≤0° C. |
| Copper Cyanide | Yes | Yes | Yes | Yes | Yes |
| Reagent for protection of TMDA | n-BuLi | n-BuLi | n-BuLi | n-BuLi | n-BuLi |
| Reagent for ortho lithiation of 3 | n-BuLi | n-PhLi | n-PhLi | n-PhLi | n-PhLi |
| Reaction solvent | Toluene | THF | MTBE | MTBE | MTBE |
| Reaction Time | Overnight | Overnight | Overnight | Overnight | Overnight |
| Comments | Small amount of product (TLC) | Small amount of product (TLC) | Major product and minor starting material (TCL) | Major product and minor starting material (TCL) | Major product and minor starting material (TCL) |

TABLE 2b

Details of experiments

| Experimental Parameters | Experiment 6 | Experiment 7 | Experiment 8 | Experiment 9 | Experiment 10 |
|---|---|---|---|---|---|
| Lot number | R-UT-1059-005 | R-UT-1059-010 | R-UT-1059-015 | R-UT-1059-021 | R-UT-1059-022 |
| Scale | 100 mg | 1.0 g | 100 mg | 500 mg | 500 mg |
| Allylating agent | Allyl iodide | Allyl iodide | Allyl iodide | Allyl iodide | Allyl iodide |
| Reaction Temp | ≤0° C. | ≤0° C. | ≤0° C. | ≤0° C. | RT |
| Copper Cyanide | Yes | Yes | Yes | Yes | Yes |
| Reagent for protection of TMDA | n-BuLi | n-BuLi | n-BuLi | n-PhLi | n-BuLi |
| Reagent for ortho lithiation of 3 | n-PhLi | n-PhLi | n-PhLi | n-PhLi | n-PhLi |
| Reaction solvent | MTBE | MTBE | MTBE | MTBE | MTBE |
| Reaction time | Overnight | Overnight | Overnight | Overnight | 6-8 hours |
| Comments | Major product and no starting material (TLC) | Yield was 50% Purification by column | Yield ~75% Purification by column | Yield ~75% Purification by column | Yield ~83% Purification by column |

TABLE 2c

Details of experiments

| Experimental Parameters | Experiment 11 | Experiment 12 | Experiment 13 | Experiment 14 |
|---|---|---|---|---|
| Lot number | R-UT-1059-030 | R-UT-1059-031 | R-UT-1059-039 | R-UT-1059-042 |
| Scale | 100 mg | 100 mg | 6.0 g | 3.0 g |
| Allylating agent | Allyl iodide | Allyl iodide | Allyl iodide | Allyl iodide |
| Reaction Temp | RT | RT | RT | RT |
| Copper Cyanide | Yes | NO | Yes | Yes |

TABLE 2c-continued

Details of experiments

| Experimental Parameters | Experiment 11 | Experiment 12 | Experiment 13 | Experiment 14 |
|---|---|---|---|---|
| Reagent for protection of TMDA | n-PhLi | n-PhLi | n-BuLi (2.5M) | n-PhLi |
| Reagent for ortho lithiation of 3 | n-PhLi (Heated to 30-35° C.) | n-PhLi (Heated to 30-35° C.) | n-PhLi (Heated to 35 ± 2° C.) | n-PhLi (Heated to 35 ± 2° C.) |
| Reaction solvent | MTBE | MTBE | MTBE | MTBE |
| Reaction time | 6-8 hours | 6-8 hours | 6-8 hours | 6-8 hours |
| Comments | Better result after heating | Trace amount of product | Product purified by distillation (7.3 g) contaminated with small amount of allylbenzene | Yield ~73% Purification by NaHSO3 method |

As illustrated from this study, synthesis of a Formula I compound was improved when ortho-lithiation is carried out at a temperature between 30° C. and 35° C. using phenyllithium or butyllithium. Furthermore, the target compound (7) was obtained in good yield and high purity when allylation is carried out at ambient temperatures, for example at room temperature.

The invention is further illustrated by, though in no way limited to, the following examples.

Examples

1. In situ Protection of Aldehyde as Lithium ((2-(dimethylamino) ethyl(methyl)amino)(3-methoxyphenyl)methanolate (6a)

A 500-mL, three-necked, round-bottom flask equipped with a mechanical stirrer and an adapter for bubbling argon was charged with N,N,N-trimethyl ethylenediamine (2.926 g) and MTBE (20 mL) under an inert atmosphere at room temperature. To this solution was added phenyl lithium or n-butyllithium (16 mL or 11.5 mL, respectively), and the reaction mixture was stirred at for 15-30 minutes at ambient temperature. A solution of 3-methoxybenzaldehyde (3, 3.0 g) in MTBE (5 mL) was then added to the flask over a period of 10-15 minutes and the reaction mixture was allowed to stir for another 20-30 minutes to generate the titled compound lithium ((2-(dimethylamino)ethyl)(methyl)amino)(3-methoxyphenyl)methanolate (6a), in situ.

2. Allylation Reaction

To the solution of the protected aldehyde was added phenyl lithium (49 mL, 1.8 M in butyl ether) drop wise over a period of 15-30 minutes. The reaction mixture was heated at 35±2° C. for 3-4 hours and then allowed to cool to room temperature. Copper cyanide (8.5 g) was then Added and the reaction mixture was stirred for 30-60 minutes at the room temperature. To the resulting suspension was added allyl iodide (9.1 mL) added drop wise over a 20-30 minute interval of time. Following the addition of allyl iodide, the reaction mixture was stirred for an additional 30-60 minutes and the progress of the allylation reaction was monitored by TLC using a mixture of dichloromethane:ethylacetate:hexane (15:85:15) as the eluting solvent. If needed, TLC plates were eluted more than once to improve resolution.

Following completion, the reaction mixture was quenched with sodium sulfite (12 g dissolved in water (30 mL)), followed by the addition of Celite (10-12 g). After stirring the reaction mixture vigorously, it was filtered through a pad of Celite, followed by a wash step using ethyl acetate. The organic layer containing the crude was washed with saturated NaHS03 (2×50 mL) solution and concentrated in vacuo.

The obtained crude product was dissolved in ethanol (50 mL). Sodium bisulfate (3.6 g) was added to the ethanolic solution and the mixture was heated at a temperature between 40-60° C. Water (25 mL) and ethyl acetate (25 mL) were added to during heating to prevent precipitation and keep the reaction mixture clear.

Following heating, the solution is cooled and the solvent removed under reduced pressure to obtain solid material. Tituration of the solid material with hexanes/MTBE (2:1 solution) removed impurities as judged by TLC. The solid material which is the sodium bisulfite adduct of the target compound (7) was isolated by filtration, dissolved in saturated sodium bicarbonate (50 mL) and extracted with ethyl acetate or MTBE (3×50 mL). The combined organic layers were washed with brine, dried over sodium sulfate, filtered and concentrated in vacuo to yield compound 7 (2.82 g, 73%).

A similar synthetic strategy (see Scheme 2), was employed to allylate 3-(benzyloxy) benzaldehyde (8). Briefly, protection of the aldehyde using N,N,N-trimethyl ethylenediamine followed by ortho-lithiation and treatment with copper cyanide generates the corresponding cuperate in situ. Allylation of the cooperate using allyl iodide followed by hydrolysis gave the target compound (9) in 70% yield.

Scheme 2

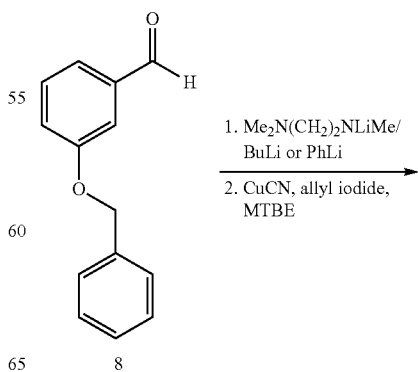

8

-continued

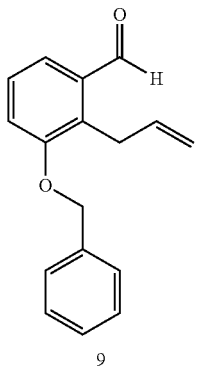

9

Inventive compounds (7) or (9) have been used to synthesize the prostacyclin analog (+)-Treprostinil.

All references and publications cited in the specification are incorporated by reference herein to the same extent as if individually incorporated by reference.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. In a process of preparing a pharmaceutical product comprising a prostacyclin, wherein the prostacyclin is synthesized from a starting material of Formula I:

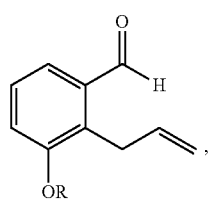

the improvement comprising:
(I) synthesizing a compound of Formula A

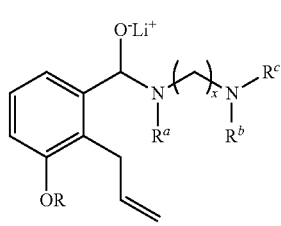

by:
(i) contacting a compound of Formula B

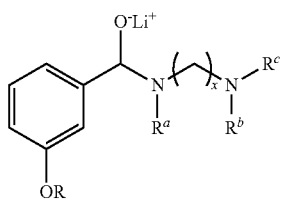

with an organolithium;
(ii) contacting the lithiated product from step (i) with copper cyanide to form a cuprate; and
(iii) contacting the cuprate from step (ii) with an allyl halide selected from the group consisting of allyl chloride, allyl bromide and allyl iodide; and (II) hydrolyzing the compound of Formula A to form the compound of Formula I, wherein,
x is an integer between 2 and 4 inclusive;
R is selected from the group consisting of straight or branched $(C_1\text{-}C_6)$alkyl, $(C_6\text{-}C_{14})$aryl, and $(C_6\text{-}C_{14})$aryl$(C_1\text{-}C_6)$alkylene-; and
$R^a$, $R^b$ and $R^c$ are each independently selected from the group consisting of straight or branched $(C_1\text{-}C_6)$ alkyl, $(C_3\text{-}C_6)$cycloalkyl, $(C_6\text{-}C_{14})$ aryl, $(C_6\text{-}C_{14})$aryl $(C_1\text{-}C_6)$alkylene, and $(C_3\text{-}C_6)$cycloalkyl$(C_1\text{-}C_6)$ alkylene-.

2. The improvement of claim 1, wherein $R^a$, $R^b$ and $R^c$ are each independently $(C_1\text{-}C_6)$alkyl.

3. The improvement of claim 2, wherein $R^a$, $R^b$ and $R^c$ are each methyl.

4. The improvement of claim 1, wherein $R^a$ is $(C_1\text{-}C_6)$ alkyl and $R^b$ and $R^c$ are each independently $(C_3\text{-}C_6)$cycloalkyl.

5. The improvement of claim 1, wherein integer x is 2.

6. The improvement of claim 1, wherein R is straight or branched $(C_1\text{-}C_6)$alkyl.

7. The improvement of claim 1, wherein R is methyl.

8. The improvement of claim 1, wherein R is $(C_6\text{-}C_{14})$ aryl$(C_1\text{-}C_6)$alkylene-.

9. The improvement of claim 1, wherein R is benzyl.

10. The improvement of claim 1, wherein the organolithium is phenyllithium, or butyllithium.

11. The improvement of claim 1, wherein said hydrolyzing comprises contacting the compound of Formula A with an agent selected from the group consisting of water, aqueous mineral acid, and an aqueous solution of sodium sulfite.

12. The improvement of claim 1, wherein said hydrolyzing comprises contacting the compound of Formula A with an aqueous solution of sodium sulfite.

13. The improvement of claim 1, wherein the prostacyclin is treprostinil.

14. In a process of preparing a pharmaceutical product comprising a prostacyclin, wherein the prostacyclin is synthesized from a starting material of Formula I:

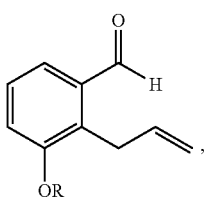

the improvement comprising:
(a) contacting an aldehyde of Formula C

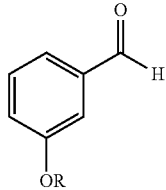

C with a compound of formula $R^cR^bN-(CHR')_x-NHR^a$ in the presence of an organolithium;
wherein
x is an integer between 0 and 4 inclusive;
R' is H,
R is an alcohol protecting group or is selected from the group consisting of straight or branched ($C_1$-$C_6$) alkyl, ($C_6$-$C_{14}$)aryl, and ($C_6$-$C_{14}$)aryl($C_1$-$C_6$)alkylene-; and $R^a$, $R^b$ and $R^c$ are each independently selected from the group consisting of straight or branched ($C_1$-$C_6$) alkyl, ($C_3$-$C_6$)cycloalkyl, ($C_6$-$C_{14}$)aryl, ($C_6$-$C_{14}$)aryl ($C_1$-$C_6$)alkylene, and ($C_3$-$C_6$)cycloalkyl($C_1$-$C_6$) alkylene-;
(b) contacting the product from step (a) with an organolithium to form an ortho-lithiated product, and then contacting the ortho-lithiated product with copper cyanide to form a cuprate;
(c) contacting the cuprate from step (b) with an allyl halide selected from the group consisting of allyl chloride, allyl bromide and allyl iodide; and
(d) hydrolyzing the product of step (c) to form the compound of Formula I.

15. The improvement of claim 14, wherein said organolithium is phenyllithium.

16. The improvement of claim 14, wherein integer x is 1 and $R^a$, $R^b$ and $R^c$ are methyl and wherein the allyl halide is allyl iodide.

17. The improvement of claim 14, wherein the prostacyclin is treprostinil.

* * * * *